United States Patent
Mackenzie

(10) Patent No.: US 8,920,518 B2
(45) Date of Patent: Dec. 30, 2014

(54) SOCKET SYSTEM INCLUDING A VACUUM LINER FOR PROSTHETIC OR ORTHOTIC DEVICES AND ASSOCIATED METHODS

(75) Inventor: Craig Mackenzie, Orlando, FL (US)

(73) Assignee: Evolution Industries, Inc., Orlando, FL (US)

(*) Notice: Subject to any disclaimer, the term of this patent is extended or adjusted under 35 U.S.C. 154(b) by 177 days.

(21) Appl. No.: 13/317,279

(22) Filed: Oct. 13, 2011

(65) Prior Publication Data

US 2012/0191217 A1 Jul. 26, 2012

Related U.S. Application Data

(60) Provisional application No. 61/455,179, filed on Oct. 15, 2010.

(51) Int. Cl.
*A61F 2/80* (2006.01)
*A61F 2/78* (2006.01)

(52) U.S. Cl.
CPC ............. *A61F 2/80* (2013.01); *A61F 2/7812* (2013.01); *A61F 2002/805* (2013.01)
USPC .......................................................... 623/36

(58) Field of Classification Search
USPC .......................................................... 623/36
See application file for complete search history.

(56) References Cited

U.S. PATENT DOCUMENTS 5,728,168 A * 3/1998 Laghi et al. ..................... 623/36
2007/0005149 A1 * 1/2007 Egilsson et al. ................ 623/34

OTHER PUBLICATIONS

Shore Durometer Conversion Chart, by Rick White of Thermal Techn Equipment Co inc, retrieved Mar. 4, 2013. http://www.ttequip.com/knowledgelibrary/TechPageShoreDurometerConversionChart.htm.*

* cited by examiner

Primary Examiner — David Isabella
Assistant Examiner — Jacqueline Woznicki
(74) Attorney, Agent, or Firm — Workman Nydegger

(57) ABSTRACT

The socket system includes a socket and a vacuum liner. A one-way valve is positioned within the closed distal end of the socket and provides controlled fluid communication between the interior socket space and an external environment. The closed distal end of the vacuum liner includes a distal portion formed of a higher durometer elastomeric material than the surrounding portions of the liner, and including a concave section extending from an external surface thereof towards the interior liner space. The socket, on the interior of the closed distal end thereof, includes a receiving portion that corresponds to and receives the distal portion of the vacuum liner 20 (e.g. matching the perimeter and depth of the distal portion). The receiving portion includes a bottom surface (e.g. a flat surface) opposite to the concave section of the vacuum liner when received therein, and defining an exterior liner space therewith.

7 Claims, 3 Drawing Sheets

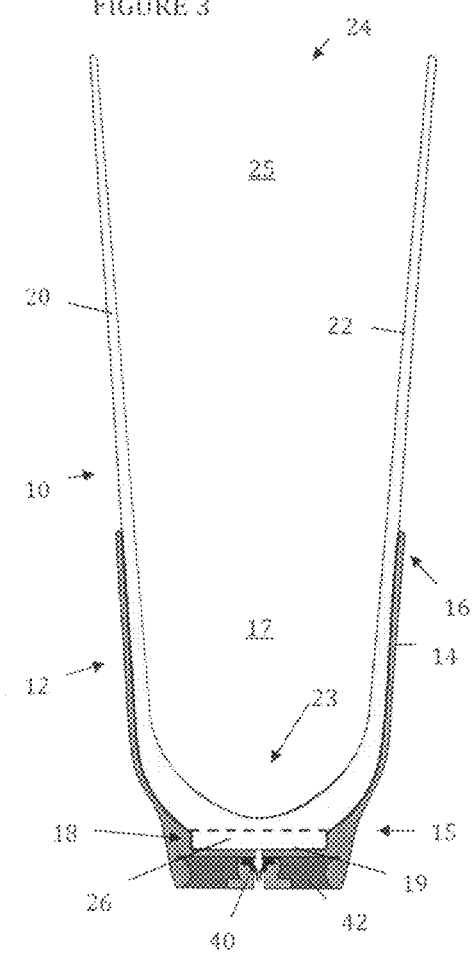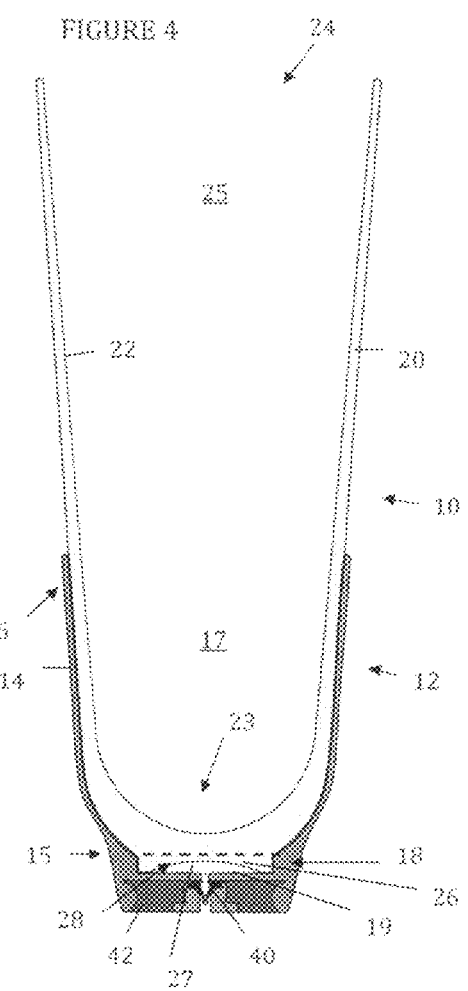

SOCKET SYSTEM INCLUDING A VACUUM LINER FOR PROSTHETIC OR ORTHOTIC DEVICES AND ASSOCIATED METHODS

RELATED APPLICATION

This application claims priority to a provisional application Ser. No. 61/455,179 filed Oct. 15, 2010, the entire disclosure of which is incorporated herein by reference.

FIELD OF THE INVENTION

The present invention relates to the field of prosthetic and orthotic liners (i.e. skin-socket interface liners), and more particularly to custom and production ("off the shelf") prosthetic liners, socket systems and associated methods.

BACKGROUND OF THE INVENTION

Liners provide a soft, flexible interface between a residual limb of an amputee and a hard socket to which a prosthetic device is secured. Such liners are typically made of an elastomeric material such as silicone. Such liners may also be used in connection with orthotic devices. Prosthetic suspension liners are described in prior patents, and may be fabricated of elastomeric or rubber materials, and are used to cushion a post-operative stump or residual limb with respect to a prosthesis that is installed over the residual limb and coupled to the liner, e.g. by a conventional locking device.

Such liners should conform closely with the residual limb, accommodate all surface contours and sub-surface bone elements of the residual limb, and provide a comfortable cushion between the residual limb and the hard socket of the prosthesis that is to be fitted over the residual limb. Various silicone rubber or elastomeric materials are used for suspension liners. Such elastomeric materials having an appropriate hardness/softness, elongation, tensile, and other properties, such as bio-inertness (resulting in no skin reaction), have been successfully used for suspension liners.

The elastomeric forming the liner frictionally engages and remains attached to the skin of a residual limb so that the limb is retained within the prosthetic socket in a comfortable, non-irritating manner. For example, liners may be used for any level of amputation both upper and lower limb. Prosthetic liners are used to cushion the amputee's residual limb from shock during ambulation.

With the advent of vacuum assisted or suction socket systems the residual limb is surrounded in a non-permeable material, and the socket is secured to the limb/liner via a vacuum link. A consequence of reduced or loss of vacuum is the possibility of losing the link between the liner and socket. A loss of linkage could result in the detachment or loss of the prosthesis.

Prior art approaches include applying external vacuum systems to the prosthesis to achieve enhanced suspension between the socket and the amputee. Such a prosthesis normally has four main suspension components. The socket is the rigid or semi-rigid structure that has a shape designed to encompass the residual limb. The liner is a softer interface between the socket and the amputees residual limb. A seal contains the vacuum between the inner surface of the socket and the outer surface of the liner, and a vacuum pump or other means introduces vacuum into the space between the inner surface of the socket and the outer surface of the liner.

SUMMARY OF THE INVENTION

It is an object of the present invention to provide a more reliable socket system, liner and/or prosthetic device that enhances vacuum in the space between the inner surface of the socket and the outer surface of the liner.

This and other objects, advantages and features in accordance with the present invention are provided by a socket system for use with a prosthetic device to be secured to a residual limb, and including a socket and a vacuum liner. The socket includes a cylindrical body having a closed distal end and an open proximal end, and defining an interior socket space to receive the residual limb and donned vacuum liner. At the distal end of the socket, a one-way valve is positioned within the closed distal end and provides controlled fluid communication between the interior socket space and an external environment.

The vacuum liner includes an elongated elastomeric tube having a closed distal end and an open proximal end, and defining an interior liner space configured to receive the residual limb. The closed distal end of the vacuum liner includes a distal portion, formed of a higher durometer elastomer material than the surrounding portions of the liner, and including a concave section extending from an external surface thereof towards the interior liner space. The distal portion may be a protrusion, e.g. disk shaped, having an outer perimeter and depth.

The socket, on the interior of the closed distal end thereof, includes a receiving portion that corresponds to and receives the distal portion of the vacuum liner (e.g. matching the perimeter and depth of the distal portion). The receiving portion includes a bottom surface (e.g. a flat surface) opposite to the concave section of the vacuum liner when received therein, and defining an exterior liner space therewith.

When the amputee walks, such exterior liner space collapses under the weight of the amputee and forces the air that was contained therein out of the socket through the one-way valve (e.g. FIG. 3). As weight is relieved from the prosthesis during swing phase, the higher durometer elastomer material of the distal portion is urged to return to its original shape, pulling air into the exterior liner space from the surrounding socket (FIG. 4). This cycle is repeated as the amputee walks removing air from the socket creating a vacuum.

The vacuum liner and higher durometer elastomer material of the distal portion can be manufactured in a two-stage pour with a corresponding mold, for example. The distal portion could also be adhered either permanently by glue or temporarily by hook and loop fastener, for example. These are just examples and other methods of making may be available and considered.

Of course, the bottom surface of the receiving portion could be flat, concave or convex depending on the desired vacuum and/or comfort of the amputee. The concave section and corresponding bottom surface could be reversed (i.e. on the closed distal end of the vacuum liner and on the interior of the closed distal end of the socket). Such configuration may result in a need to extend the length of the socket. The one-way valve is configured to allow the weight of a user, via the residual limb, to expel air from the interior socket space out to the external environment. The one-way valve may be a duckbill valve, for example, and/or have a cracking pressure of about 0.2 psi.

Objects, advantages and features in accordance with the present invention are also provided by a vacuum liner for use with a socket and associated prosthetic device to be secured to a residual limb. The socket includes a cylindrical body having a closed distal end and an open proximal end, and defining an interior socket space to receive the residual limb and donned vacuum liner. At the distal end of the socket, a one-way valve is positioned within the closed distal end and provides controlled fluid communication between the interior socket space and an external environment.

The vacuum liner includes an elongated elastomeric tube having a closed distal end and an open proximal end, and defining an interior liner space configured to receive the residual limb. The closed distal end of the vacuum liner includes a distal portion, formed of a higher durometer elastomer material than the surrounding portions of the liner, and including a concave section extending from an external surface thereof towards the interior liner space. The distal portion may be a protrusion, e.g. disk shaped, having an outer perimeter and depth.

The distal portion of the vacuum liner is configured to be received in the socket, on the interior of the closed distal end thereof that includes a corresponding receiving portion (e.g. matching the perimeter and depth of the distal portion). The concave section of the vacuum liner is configured to define an exterior liner space when opposite a bottom surface (e.g. a flat surface) of the receiving portion of the socket.

Objects, advantages and features in accordance with the present invention are also provided by a method of making a socket system for use with a prosthetic device to be secured to a residual limb, and including providing a socket and providing a vacuum liner. Providing the socket includes forming a cylindrical body having a closed distal end and an open proximal end, and defining an interior socket space to receive the residual limb and donned vacuum liner. At the distal end of the socket, a one-way valve is positioned within the closed distal end and provides controlled fluid communication between the interior socket space and an external environment.

Providing the vacuum liner includes forming an elongated elastomeric tube having a closed distal end and an open proximal end, and defining an interior liner space configured to receive the residual limb. The closed distal end of the vacuum liner includes a distal portion, formed of a higher durometer elastomer material than at least the surrounding portions of the liner, and including a concave section extending from an external surface thereof towards the interior liner space. The distal portion may be a protrusion, e.g. disk shaped, having an outer perimeter and depth.

The socket, on the interior of the closed distal end thereof, is formed to include a receiving portion that corresponds to and receives the distal portion of the vacuum liner (e.g. matching the perimeter and depth of the distal portion). The receiving portion includes a bottom surface (e.g. a flat surface) opposite to the concave section of the vacuum liner when received therein, and defining an exterior liner space therewith.

BRIEF DESCRIPTION OF THE DRAWING

FIGS. 3 and 4 are cross-sectional views of a socket system including the vacuum liner of FIG. 1 in accordance with features of an embodiment of the present invention.

DETAILED DESCRIPTION OF THE PREFERRED EMBODIMENTS

The present invention will now be described more fully hereinafter with reference to the accompanying drawings in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The dimensions of layers and regions may be exaggerated in the figures for ease of explanation.

The following description refers to, by example, a liner associated with a lower limb (e.g. the knee), however, the features of the invention apply to liners for use with any limb/joint area that may benefit from the use of vacuum assistance as described herein. Features of the present invention are directed to a prosthetic liner and associated methods of making and using, and includes the use of an elastomeric material, e.g. pourable or injectable silicone, that may be used with a simple mold or press. The silicone is preferably biocompatible, e.g. "healthcare grade" or "medical grade", which is suitable for external use. For example, an appropriate silicone system may also be clear to semi-translucent and curable at room temperature. The molded silicone liner should have high tear strength and exhibit flexibility and high elasticity. Other elastomers or materials exhibiting the necessary qualities of a skin-interface liner may also be used.

Figure 1:
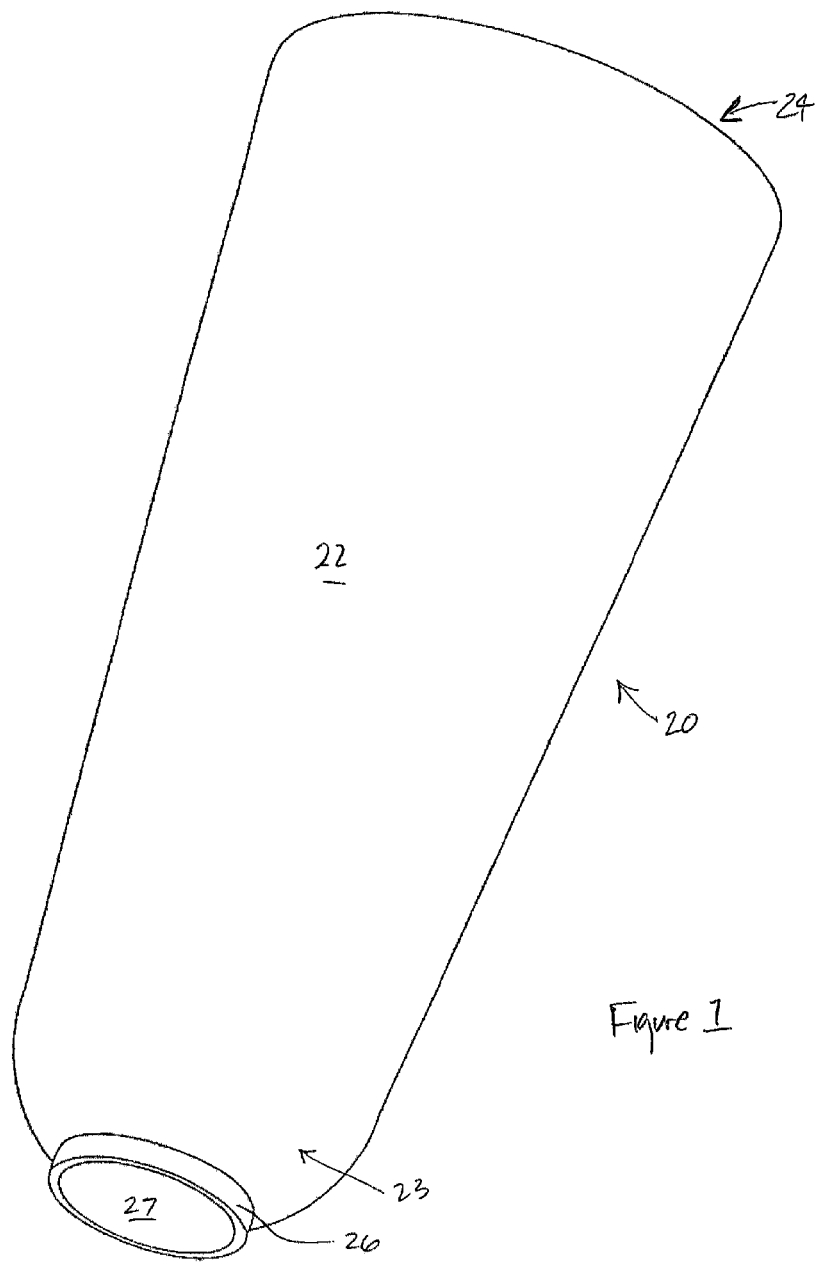
FIG. 1 is a perspective view of the vacuum liner in accordance with features of an embodiment of the present invention.
Figure 2:
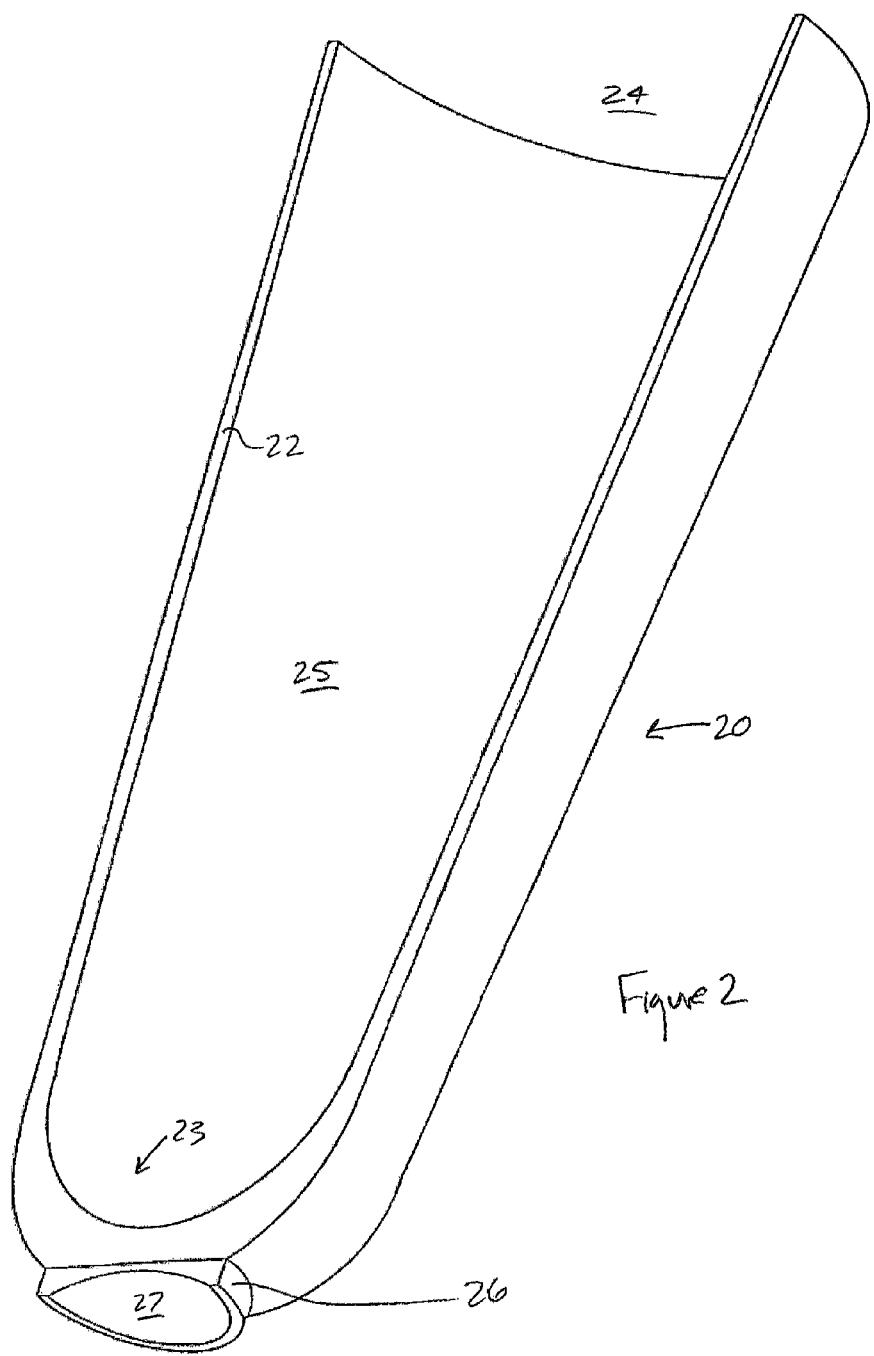
FIG. 2 is a cross-sectional perspective view of the vacuum liner of FIG. 1.

Referring to FIGS. 1-4, the approach of the present invention will be described. It is an object of the present invention to provide a more reliable socket system 10, liner 20 and/or associated prosthetic device that enhances vacuum in the space between the inner surface of the socket 12 and the outer surface of the liner 20.

This and other objects, advantages and features in accordance with the present invention are provided by a socket system 10 for use with a prosthetic device to be secured to a residual limb, and including a socket 12 and a vacuum liner 20. The socket 12 includes a cylindrical body 14 having a closed distal end 15 and an open proximal end 16, and defining an interior socket space 17 to receive the residual limb and donned vacuum liner 20. At the distal end 15 of the socket 12, a one-way valve 40 is positioned within the closed distal end and provides controlled fluid communication between the interior socket space 17 and an external environment.

A mounting plate 42 may also be included in the distal end 15, as would be appreciated by those skilled in the art. A vacuum seal (not shown) may also be provided adjacent the proximal end 16 of the socket adjacent and/or on an interior or exterior surface thereof, as would also be appreciated by those skilled in the art.

The vacuum liner 20 includes an elongated elastomeric tube 22 having a closed distal end 23 and an open proximal end 24, and defining an interior liner space 25 configured to receive the residual limb. The elastomeric tube 22 of the liner 20 is formed of an elastomeric material having an appropriate durometer. The liner 20 is donned by an amputee with the closed end 23 adjacent and preferably in close contact with a distal end of the residual limb. The closed distal end 23 of the vacuum liner 20 includes a distal portion 26, formed of a higher durometer elastomeric material than the surrounding portions of the liner 20, and including a concave section 27 extending from an external surface thereof towards the interior liner space 25. The distal portion 26 may be a protrusion, e.g. disk shaped, having an outer perimeter and depth.

For example, the durometer hardness of the elastomeric tube 22 may be between 38-55 while the durometer hardness of the distal portion 26 may be between 60-90 on the Shore-OO scale. The durometer hardness of the relative areas may vary depending upon patient weight and potential activity level.

The socket 12, on the interior of the closed distal end 15 thereof, includes a receiving portion 18 that corresponds to and receives the distal portion 26 of the vacuum liner 20 (e.g. matching the perimeter and depth of the distal portion). The receiving portion 18 includes a bottom surface 19 (e.g. a flat surface) opposite to the concave section 27 of the vacuum liner 20 when received therein, and defining an exterior liner space 28 therewith.

When the amputee walks, such exterior liner space 28 collapses under the weight of the amputee and forces the air that was contained therein out of the socket 12 through the one-way valve 40 (e.g. FIG. 3). As weight is relieved from the prosthesis during the swing phase, the higher durometer elastomeric material of the distal portion 26 is urged to return to its original shape, pulling air into the exterior liner space 28 from the surrounding socket (FIG. 4). This cycle is repeated as the amputee walks removing air from the socket creating a vacuum. Thus, the distal portion 26 and concave section 27 of the vacuum liner 20 in combination with the receiving portion 18 and bottom surface 19 of the socket 12, define a vacuum pump.

The vacuum liner 20 and higher durometer elastomeric material of the distal portion 26 can be manufactured in a two-stage pour with a corresponding mold, for example. In other words, the elastomeric tube 22 and distal portion 26 are preferably integrally formed as a monolithic unit. The distal portion 26 could also be adhered either permanently by glue or temporally by hook and loop fastener, for example. These are just examples and other methods of making may be available and considered.

Of course, the bottom surface 19 of the receiving portion 18 could be flat, concave or convex depending on the desired vacuum and/or comfort of the amputee. The concave section 27 and corresponding bottom surface 19 could be reversed (i.e. on the closed distal end 23 of the vacuum liner 20 and on the interior of the closed distal end 15 of the socket 12). Such configuration may result in a need to extend the length of the socket. The one-way valve 40 is configured to allow the weight of a user, via the residual limb, to expel air from the interior socket space, i.e. from the interface between the outer surface of the liner 20 and the inner surface of the socket 12, out to the external environment.

A type of one-way valve 20 is a duckbill valve which is made of rubber and has a low cracking pressure, about 0.2 psi. Other types of one-way valves are also available and may be used in the present approach. The one-way valve 40 should not allow air, moisture or any other contaminate to enter the interior space 17 of the socket 12.

Objects, advantages and features in accordance with the present invention are also provided by a vacuum liner 20 for use with a socket 12 and associated prosthetic device to be secured to a residual limb.

The vacuum liner 20 includes an elongated elastomeric tube 22 having a closed distal end 23 and an open proximal end 24, and defining an interior liner space 25 configured to receive the residual limb. The closed distal end 23 of the vacuum liner includes a distal portion 26, formed of a higher durometer elastomeric material than the surrounding portions of the liner 20, and including a concave section 27 extending from an external surface thereof towards the interior liner space 25. The distal portion 26 may be a protrusion, e.g. disk shaped, having an outer perimeter and depth.

The distal portion 26 of the vacuum liner 20 is configured to be received in the socket 12 on the interior of the closed distal end 15 thereof that includes a corresponding receiving portion 18 (e.g. matching the perimeter and depth of the distal portion). The concave section 27 of the vacuum liner 20 is configured to define an exterior liner space 28 when opposite a bottom surface 19 (e.g. a flat surface) of the receiving portion 18 of the socket 12.

Objects, advantages and features in accordance with the present invention are also provided by a method of making a socket system 10 for use with a prosthetic device to be secured to a residual limb, and including providing a socket 12 and providing a vacuum liner 20. Providing the socket 12 includes forming a cylindrical body 14 having a closed distal end 15 and an open proximal end 16, and defining an interior socket space 17 to receive the residual limb and donned vacuum liner 20. At the distal end 15 of the socket 12, a one-way valve 40 is positioned within the closed distal end and provides controlled fluid communication between the interior socket space 17 and an external environment.

Providing the vacuum liner 20 includes forming an elongated elastomeric tube 22 having a closed distal end 23 and an open proximal end 24, and defining an interior liner space 25 configured to receive the residual limb. The closed distal end 23 of the vacuum liner 20 includes a distal portion 26 formed of a higher durometer elastomeric material than at least the surrounding portions of the liner 20, and including a concave section 27 extending from an external surface thereof towards the interior liner space. The distal portion 26 may be a protrusion, e.g. disk shaped, having an outer perimeter and depth.

The socket 12, on the interior of the closed distal end 15 thereof, is formed to include a receiving portion 18 that corresponds to and receives the distal portion 26 of the vacuum liner 20 (e.g. matching the perimeter and depth of the distal portion). The receiving portion 18 includes a bottom surface 19 (e.g. a flat surface) opposite to the concave section 27 of the vacuum liner 20 when received therein, and defining an exterior liner space 28 therewith.

Thus, the weight of the amputee during ambulation will create enough force to push or expel air out of the interior socket space through the one-way valve 40 keeping the residual limb secured to the socket 12 via an associated vacuum link.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A vacuum liner for use with a prosthetic device to be secured to a residual limb, the vacuum liner comprising:
   an elongated elastomeric tube having a closed distal end and an open proximal end, and defining an interior liner space configured to receive the residual limb;
   the closed distal end including a distal portion formed of a higher durometer elastomeric material than surrounding portions of the elastomeric tube;
   wherein the distal portion defines a disk shaped protrusion having a perimeter and includes an exterior liner space defined by a recessed concave surface formed by a depth into the higher durometer elastomeric material, the recessed concave surface extending from an external end-surface of the distal portion adjacent to the perimeter and towards the interior liner space;
   wherein the distal portion is sized and configured for mating against a surrounding socket so that as weight is applied to the socket, the exterior liner space collapses due to applied weight and forces air contained out of the socket, when weight is relieved from the socket, the higher durometer elastomeric material of the distal portion is urged to return to its original shape, pulling air into the exterior liner space from the surrounding socket.

2. The vacuum liner according to claim 1 wherein a durometer hardness of the elastomeric tube is between 38-55 while a durometer hardness of the distal portion is between 60-90 on the Shore-OO scale.

3. The vacuum liner according to claim 1 wherein the distal portion and concave section defining at least part of vacuum pump are integrally formed with the elongated elastomeric tube as a monolithic unit.

4. A method of making a vacuum liner for use with a prosthetic device to be secured to a residual limb, the method comprising:
   forming an elongated elastomeric tube having a closed distal end and an open proximal end, and defining an interior liner space configured to receive the residual limb;
   forming the closed distal end to include a distal portion of a higher durometer elastomeric material than surrounding portions of the elastomeric tube;
   forming the distal portion as defining a disk-shaped protrusion having a perimeter and includes an exterior liner space defined by a recessed concave surface formed by a depth into the higher durometer elastomeric material and extending from an external end-surface of the distal portion adjacent to the perimeter and towards the interior liner space;
   wherein the distal portion is sized and configured for mating against a surrounding socket so that as weight is applied to the socket, the exterior liner space collapses due to applied weight and forces air contained out of the socket, when weight is relieved from the socket, the higher durometer elastomeric material of the distal portion is urged to return to its original shape, pulling air into the exterior liner space from the surrounding socket.

5. The method according to claim 4 wherein a durometer hardness of the elastomeric tube is between 38-55 while a durometer hardness of the distal portion is between 60-90 on the Shore-OO scale.

6. A vacuum liner for use with a prosthetic device to be secured to a residual limb, the vacuum liner comprising:
   an elongated elastomeric tube having a closed distal end and an open proximal end, and defining an interior liner space configured to receive the residual limb between the open proximal end and the closed distal end;
   the closed distal end defining a distal end portion forming an annular protrusion extending distally outwardly from the liner and an exterior liner space defining a recess extending inwardly from an exterior surface of the end portion adjacent to the perimeter and into a thickness of the closed distal end short of the interior liner space such that the thickness of the closed distal end separates the recess from the interior liner space;
   wherein the distal portion is sized and configured for mating against a surrounding socket so that as weight is applied to the socket, the exterior liner space collapses due to applied weight and forces air contained out of the socket, when weight is relieved from the socket, the higher durometer elastomeric material of the distal portion is urged to return to its original shape, pulling air into the exterior liner space from the surrounding socket.

7. The vacuum liner of claim 6, wherein the recess has a concave profile.

* * * * *